US010987498B2

(12) United States Patent
Llaneza et al.

(10) Patent No.: US 10,987,498 B2
(45) Date of Patent: Apr. 27, 2021

(54) ANAL AND PERIANAL THERAPEUTIC SUBSTANCE DELIVERY DEVICE

(71) Applicant: LK Innovations, LLC, Miami, FL (US)

(72) Inventors: Pedro P. Llaneza, Miami, FL (US); Matthew Solar, Melbourne, FL (US)

(73) Assignee: LK Innovations, LLC, Miami, FL (US)

( * ) Notice: Subject to any disclaimer, the term of this patent is extended or adjusted under 35 U.S.C. 154(b) by 34 days.

(21) Appl. No.: 16/270,708

(22) Filed: Feb. 8, 2019

(65) Prior Publication Data
US 2019/0247632 A1 Aug. 15, 2019

Related U.S. Application Data

(60) Provisional application No. 62/628,589, filed on Feb. 9, 2018.

(51) Int. Cl.
A61M 25/10 (2013.01)
A61M 31/00 (2006.01)

(52) U.S. Cl.
CPC ....... A61M 31/00 (2013.01); A61M 25/10186 (2013.11); A61M 2210/1067 (2013.01)

(58) Field of Classification Search
CPC .......... A61M 2210/1067; A61M 25/10; A61M 25/10186; A61M 31/00
See application file for complete search history.

(56) References Cited

U.S. PATENT DOCUMENTS

| 1,537,992 | A | | 5/1925 | Gearon |
| 2,333,342 | A | * | 11/1943 | Slocumb .................. A61J 3/08 604/287 |
| 3,459,175 | A | | 8/1969 | Miller |
| 3,760,804 | A | | 9/1973 | Higuchi et al. |
| 3,777,755 | A | | 12/1973 | Groves |
| 3,929,132 | A | | 12/1975 | Higuchi |
| 3,939,842 | A | | 2/1976 | Harris |
| 4,563,182 | A | | 1/1986 | Stoy et al. |
| 5,085,650 | A | | 2/1992 | Giglio |
| 5,192,266 | A | | 3/1993 | Wilk |
| 5,419,763 | A | | 5/1995 | Hildebrand |
| 5,700,286 | A | | 12/1997 | Tartaglia et al. |
| 6,364,852 | B1 | | 4/2002 | Lee |
| 7,465,295 | B2 | | 12/2008 | Bergeron et al. |

(Continued)

FOREIGN PATENT DOCUMENTS

CN 201353368 Y 12/2009
WO WO93/15788 A1 8/1993

(Continued)

OTHER PUBLICATIONS

International Search Report and Written Opinion of international application No. PCT/US19/16795 dated May 7, 2019.

Primary Examiner — Deanna K Hall
(74) Attorney, Agent, or Firm — Gordon & Jacobson, P.C.

(57) ABSTRACT

A device is provided for delivery of a therapeutic agent to the anal and perianal regions. The device includes a deployable internal anchor adapted to comfortably anchor the device in the anal canal, a shaft adapted to store and release the agent to the anal canal, and an external bumper adapted to store and release the agent to the perianal tissue and externally anchor the device.

20 Claims, 11 Drawing Sheets

(56) References Cited

U.S. PATENT DOCUMENTS

| | | |
|---|---|---|
| 8,016,742 B2 | 9/2011 | Whalen et al. |
| 8,480,647 B2 | 7/2013 | Shohat et al. |
| 8,715,706 B2 | 5/2014 | Barak |
| 9,005,108 B2 | 4/2015 | Uhland et al. |
| 9,227,042 B2 | 1/2016 | Gardner et al. |
| 9,555,239 B2 | 1/2017 | Caccia |
| 9,775,980 B2 | 10/2017 | Macy, Jr. et al. |
| 2002/0082679 A1 | 6/2002 | Sirhan et al. |
| 2003/0153881 A1 | 8/2003 | Roche et al. |
| 2006/0184109 A1 | 8/2006 | Gobel |
| 2006/0217637 A1 | 9/2006 | Leiboff et al. |
| 2007/0010785 A1 | 1/2007 | Sekiguchi et al. |
| 2009/0216071 A1 | 8/2009 | Zipper |
| 2012/0123185 A1 | 5/2012 | Isham |
| 2012/0221012 A1 | 8/2012 | Blurton |
| 2014/0074066 A1 | 3/2014 | Barak |
| 2014/0155846 A1 | 6/2014 | Choularton |
| 2014/0288491 A1 | 9/2014 | Halskov et al. |
| 2014/0296832 A1* | 10/2014 | Karmazyn ............ A61F 2/0009 604/514 |
| 2015/0126968 A1 | 5/2015 | Abhishek et al. |
| 2016/0184143 A1 | 6/2016 | Hooi |
| 2016/0367747 A1 | 12/2016 | Loske |
| 2017/0341848 A1 | 11/2017 | Py et al. |

FOREIGN PATENT DOCUMENTS

| | | | |
|---|---|---|---|
| WO | WO2005/020960 A1 | 3/2005 | |
| WO | WO2016/102067 A1 | 6/2016 | |

\* cited by examiner

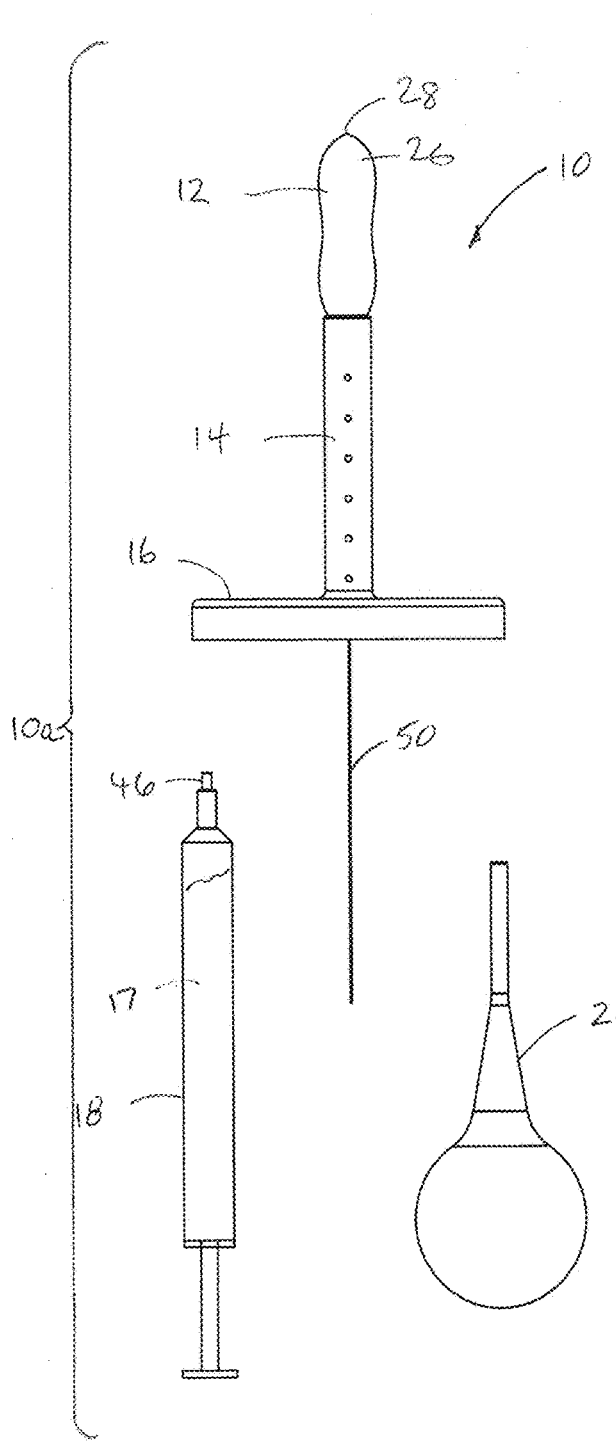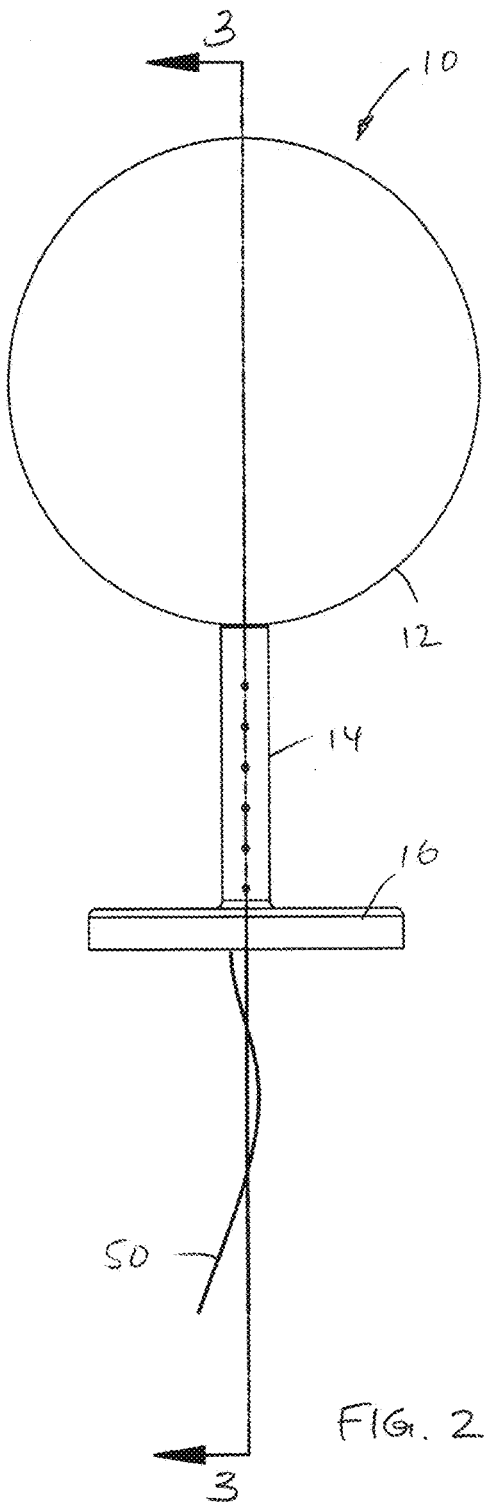
FIG. 1
FIG. 2

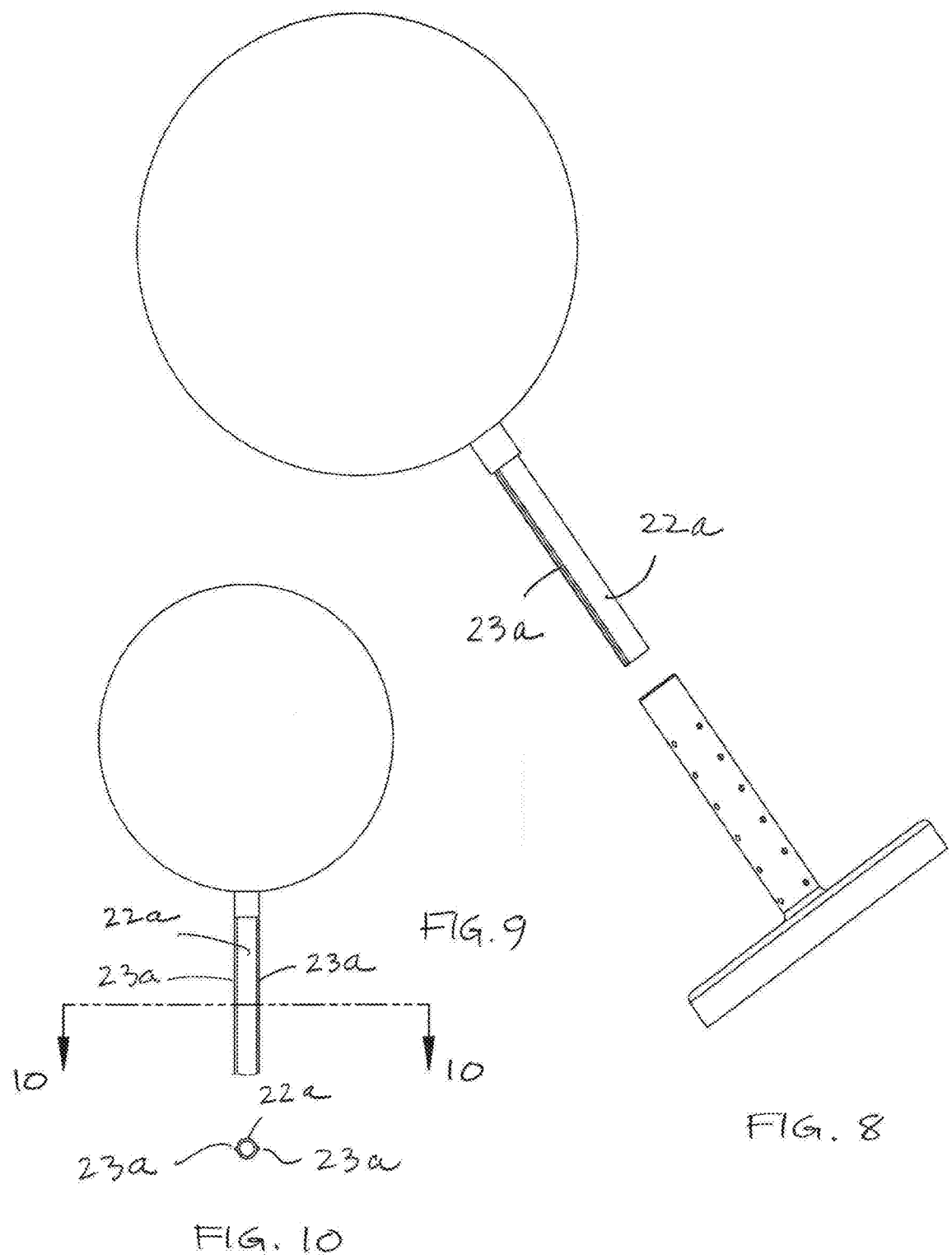

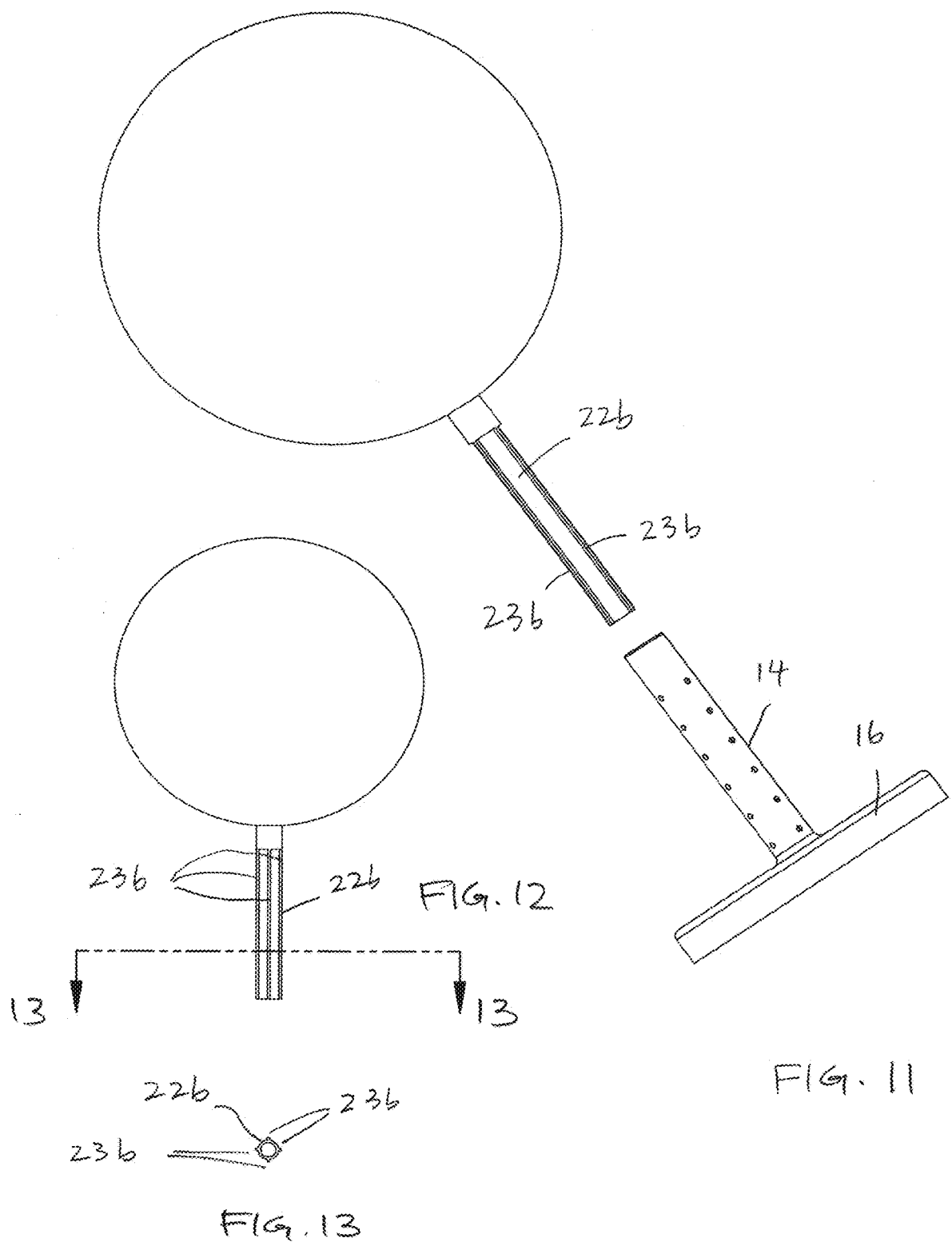

ANAL AND PERIANAL THERAPEUTIC SUBSTANCE DELIVERY DEVICE

BACKGROUND OF THE INVENTION

1. Field of the Invention

The present invention relates to a delivery device for a therapeutic and non-therapeutic agent or substance. More particularly, the invention relates to a device that temporarily delivers one or more of such agents or substances to or through the anal and perianal regions.

2. State of the Art

Most medical and non-therapeutic treatments of anal and perianal ailments and disorders rely on ointments, creams, suppositories or injections that do not provide an appropriate, constant, reliable and predictable release of substances or medicines to achieve a desirable effect. There is a need to provide a local or systemic constant release and application of a substance to achieve desired effects in this area or systemically.

SUMMARY OF THE INVENTION

In accord with the devices disclosed herein, a device for delivery of a therapeutic or non-therapeutic agent or substance (collectively "agent") to the anal and perianal regions is provided. The delivery device includes a deployable internal anchor adapted to comfortably anchor the device in the anal canal, a shaft adapted to store and release the agent to the anal canal, and an external bumper adapted to store and release the agent to the perianal tissue and externally anchor the device. The device optionally may be provided with a quantity of releasable agent in a suitable form, and an anchor expander.

In embodiments, the internal anchor is an inflatable balloon, a user-deployable retention structure, or an automatically deployable retention structure. The balloon may be inflated through a proximal valve. The deployable retention structure can include one or more retainers that are stored or positioned in the shaft and then advanced out of the shaft into an expanded state. Such retainers may be a silicone, a non-irritating polymer, a spring metal, or a heat-activated shape memory alloy. The deployment may be effected by user-applied force, spring-activation, heat-activation, or other means.

The shaft includes an agent storage portion and a system to release the agent into surrounding tissues. In an embodiment, the storage portion is a reservoir, and the release system includes a porous membrane defining an outer surface of the reservoir. The pores of the porous membrane may be filled or covered with a heat-activated material, such as a gel, resin or wax, that melts when the shaft is inserted into the anal canal to allow the agent to be released from the storage portion. In another embodiment, the porous membrane may be covered with an impermeable sheet that is removed after the storage portion is filled and prior to inserting the device into the anal canal. In another embodiment, the reservoir is filled after the device is inserted into the anal canal and the agent is permitted to release immediately. In such case, no filler or cover is provided for the porous membrane. In another embodiment, the storage portion includes surface area of the shaft and the agent is applied to the external surface of the shaft. Strips that are loaded with the agent may be provided, and the strips may be pre-attached to the external surface or provided with, for example, an adhesive backing that attaches the strips to the external surface.

The external bumper functions substantially the same as the shaft to release the agent at the perianal tissue. The bumper also includes an agent storage portion and a system to release the agent into contacting tissues. The storage portions in the bumper and shaft may be in communication with each other and the external surface of the bumper may be defined by a common porous membrane defining the outer surface of both the bumper and the shaft, and use similar or dissimilar agent release systems. The porous membrane can include any openings suitable to allow an agent to diffuse out of the reservoir to have a desired effect on the patient. The size of the porosity can be used to control the release rate of the agent from the reservoir. The pores can be relatively large openings to small micropores, which allow the agent to essentially diffuse out of the reservoir.

Where the device has an internal storage portion, the bumper includes an injection port for the injection of the agent. The internal storage portion can be divided into multiple compartments, each for receiving a different type of agent or concentration of agent.

The device also includes a proximal valve through which an inflation medium can be injected for expansion of the balloon. A tether is attached adjacent to the valve. The tether operates to open the valve to release the inflation medium from the balloon, and as a security device for the removal of the device from the patient.

One anticipated use is for the device to be used to treat anal fissures and/or hemorrhoids. For such treatment, the agent can include one or more of a pain relief agent, an anti-inflammatory agent, and a muscle relaxant. It is further anticipated that the device can be used to deliver drugs systemically, particularly where a patient's condition indicates that the anal mucosa and underlying vasculature may be a suitable pathway for delivery of the agent. For example, the device can deliver pain relievers, fever reducers, and anesthetics. Additionally, the device can be used to deliver nutrients and herbal remedies. Moreover, any agent currently delivered via suppositories can be delivered by the device described herein. It is also anticipated that the device can be used to deliver systemic therapeutic and non-therapeutic agents to patients that are unconscious, such as those that are in a coma.

BRIEF DESCRIPTION OF THE DRAWINGS

FIG. 1 is a side elevation of a system including a agent delivery device in a non-expanded configuration, an agent, and an inflation device.

FIG. 2 is a side elevation of the agent delivery device in an expanded configuration.

FIG. 8 is an exploded view of a second embodiment of the agent delivery device in the expanded configuration.

FIG. 9 is a longitudinal section view of the inflation member of the device in FIG. 8.

FIG. 10 is a section view across line 10-10 in FIG. 9.

FIG. 11 is an exploded view of a third embodiment of the agent delivery device in the expanded configuration.

FIG. 12 is a longitudinal section view of the inflation member of the device in FIG. 11.

FIG. 13 is a section view across line 13-13 in FIG. 12.

DETAILED DESCRIPTION OF THE PREFERRED EMBODIMENTS

Figure 4:
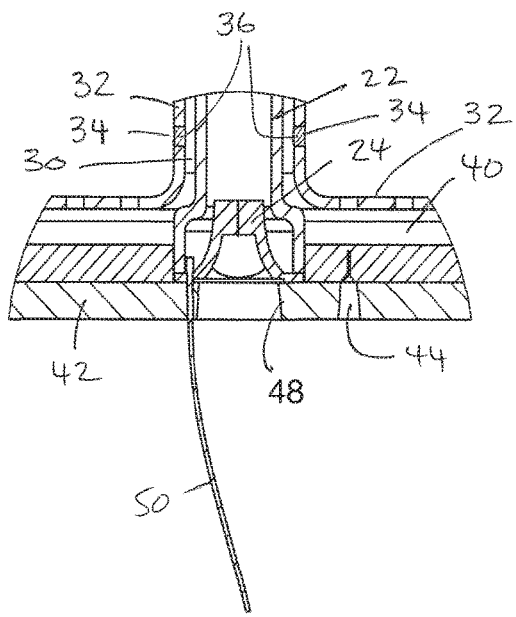
FIG. 4 is an enlarged section view of a proximal portion of the agent delivery device.

Turning now to FIGS. 1 through 4, a device 10 for delivery of a flowable agent to the anal and perianal tissues of a patient is provided. The delivery device 10 includes a deployable internal anchor 12 adapted to comfortably anchor the device in the anal canal, a shaft 14 adapted to store and release the agent to the anal canal, and an external bumper 16 adapted to store and release the agent to the perianal tissue and externally anchor the device. The device 10 optionally may be in a system 10a provided with a quantity of the agent 17 in a suitable form, such as a syringe 18, and an anchor expander, such as a fluid bulb 20.

In an embodiment of the delivery device 10, the internal anchor 12 is an inflatable balloon. The balloon 12 includes a proximally extending stem 22, and a valve 24 that opens into the stem, described further below. The balloon 12 may be compliant or non-compliant, and is preferably adapted to automatically collapse when empty of an inflation medium, and expand to a suitable size that operates to retain the device in the anal canal when inflated. The balloon may be made of a biodegradable material. Exemplar expanded sizes for the balloon 12 to anchor the device is 3 to 6 cm; other sizes may also be implemented. The inflation medium can be a liquid or gas. By way of example only, the inflation medium can be saline solution or air. When collapsed, a distal end 26 of the internal anchor presents a smooth, rounded, and atraumatic insertion tip 28. When expanded, the balloon 12 is larger in diameter than the shaft 14.

Figure 3:
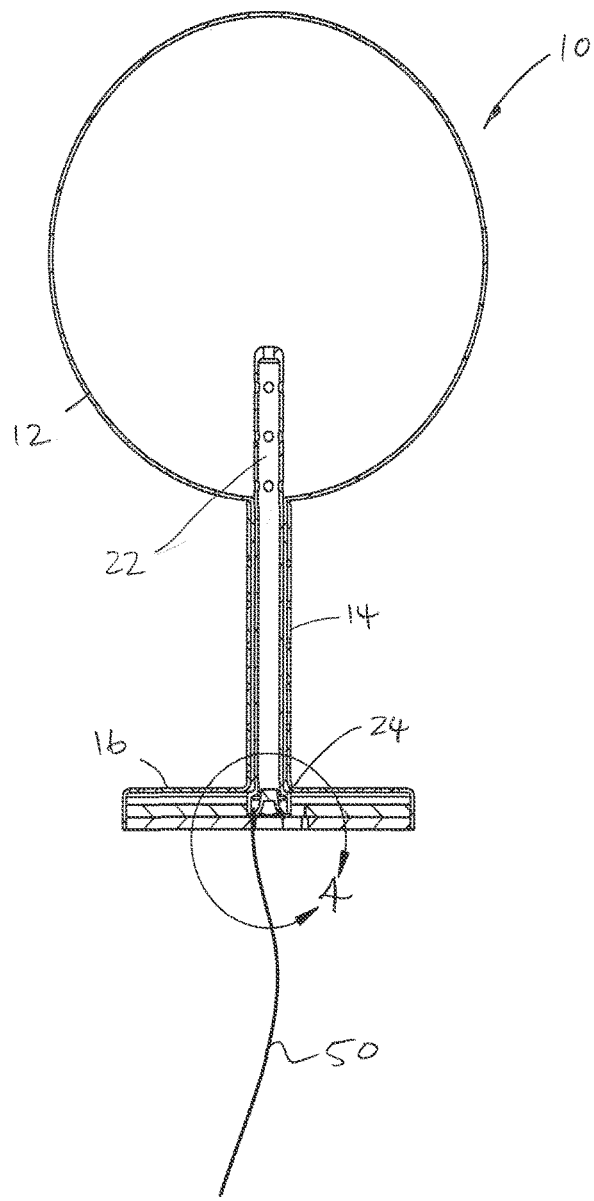
FIG. 3 is a longitudinal section view across line 3-3 in FIG. 2 of the agent delivery device in the expanded configuration.

Referring to FIGS. 3 and 4, the shaft 14 is hollow, including an agent storage portion 30 and a system or means by which to release the agent into tissue contact. In one exemplar embodiment, the shaft 14 has a length of 3.5 cm between its proximal and distal ends; i.e., between the internal anchor 12 and the bumper 16, and defines a longitudinal axis along such length and a diameter transverse to its longitudinal axis. As shown in FIGS. 3 and 4, the storage portion is a reservoir 30 defined by a soft, porous membrane 32 surrounding the stem 22 and defining an outer surface of the reservoir. The membrane 32 may be made from silicone or other porous materials. The pores 34 of the porous membrane may be pre-filled or pre-covered with a heat-activated material 36, such as a gel, resin or wax, that melts when insertion tip 28 and the shaft 14 are inserted into the anal canal; i.e., at body temperature, to allow the flowable agent to be released from the reservoir 30 and out through the pores 34.

The external bumper 16 is preferably oriented substantially orthogonal to the longitudinal axis of the shaft 14, and joins the shaft at the center of the bumper. The bumper 16 may be circular or any other shape that prevents inward migration of the device into anus and preferably provides comfort to the patient. The bumper 16 may have a same or different hardness and flexibility than the shaft. In one exemplar embodiment, the bumper 16 is 4 cm in diameter or other largest dimension (each of which is considered a 'diameter' for purposes herein). In an embodiment, the bumper 16 functions to supply and release agent at the external perianal tissue and also to prevent migration of the device 10 into the rectal vault. Similar to the shaft 14, the bumper 16 includes an agent storage portion 40 and a system to release the agent into contacting tissues. The storage portions 30, 40 in the shaft and bumper may be in communication with each other and the external surface of the bumper may be defined by a common porous membrane 32 defining the outer surface of both the bumper and the shaft, and use similar or dissimilar agent release systems. A proximal end 42 of the bumper 16, enclosing its storage portion 40, includes an injection port 42 for the injection of the agent into the reservoir. The injection port 44 is adapted to snugly receive the tip 46 of the syringe 18 carrying the agent 17 to facilitate filling the storage portions 30, 40. The bumper 16 may be constructed to have no storage portion; or even when provided with a storage portion 40, provided with no agent therein or thereon.

Figure 7:
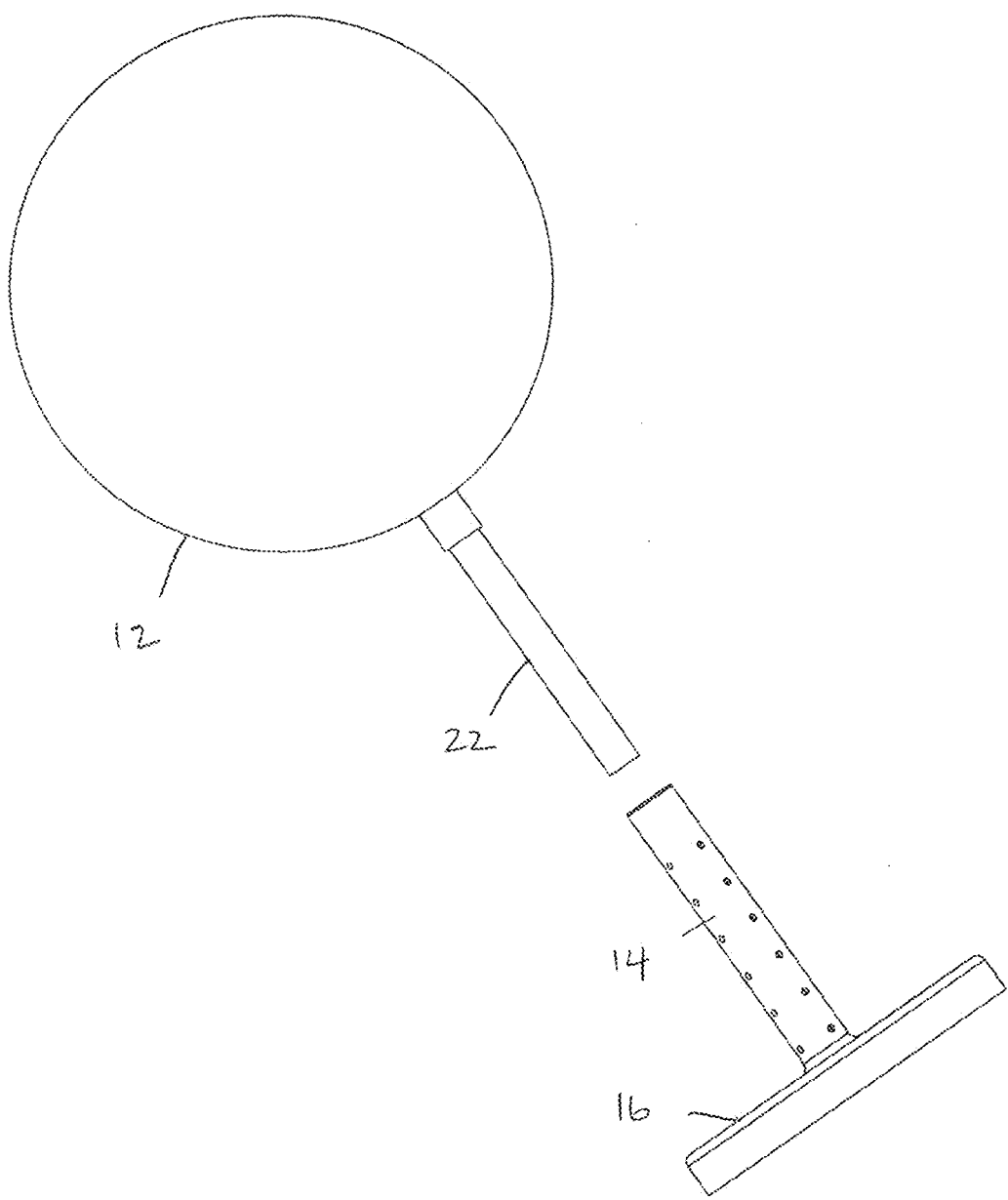
FIG. 7 is an exploded view of the agent delivery device in the expanded configuration.

Referring to FIG. 7, an exemplar assembly of the balloon 12 with stem 22 (assembled as one piece) is shown relative to the shaft 14 and bumper 16 (a unitary piece). The common reservoir of the storage portions 30, 40 is defined as the space around the stem 22 and within the shaft 14 (reservoir 30) and around the stem 22 and within the bumper 16 (reservoir 40).

Alternatively, the storage portions 30, 40 in the shaft and bumper may be separated into discrete portions such that different agents may be provided for separately dispensing to the anal canal and the perianal tissue. In such manufacture, separate injection ports may be provided for the separate storage portions. Turning to FIGS. 8 through 10, the stem 22a is provided with two longitudinal spines 23a that once inserted into and assembled relative to shaft and bumper operate to define two reservoirs about the stem. By way of another example, referring to FIGS. 11 through 13, the stem 22b is provided with four spines 23b that once inserted into and assembled relative to shaft and bumper operate to define four reservoirs about the stem.

Turning back to FIGS. 1 through 4, the proximal valve 24, preferably accessed through an opening 48 in the proximal end 42 of the bumper 16, is adapted to permit injection of an inflation medium for expansion of the balloon. For that purpose, the tip of the inflation bulb 20 and the opening 48 are adapted and configured to be snugly fit together so that the inflation medium is effectively transferred under pressure from the inflation bulb 20, through the valve 24 and into the balloon 12.

Figure 26:
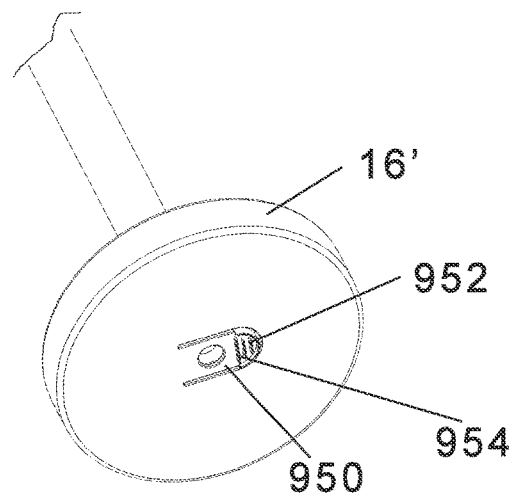
FIG. 26 is a bottom perspective view of another embodiment of an agent delivery device.
Figure 5:
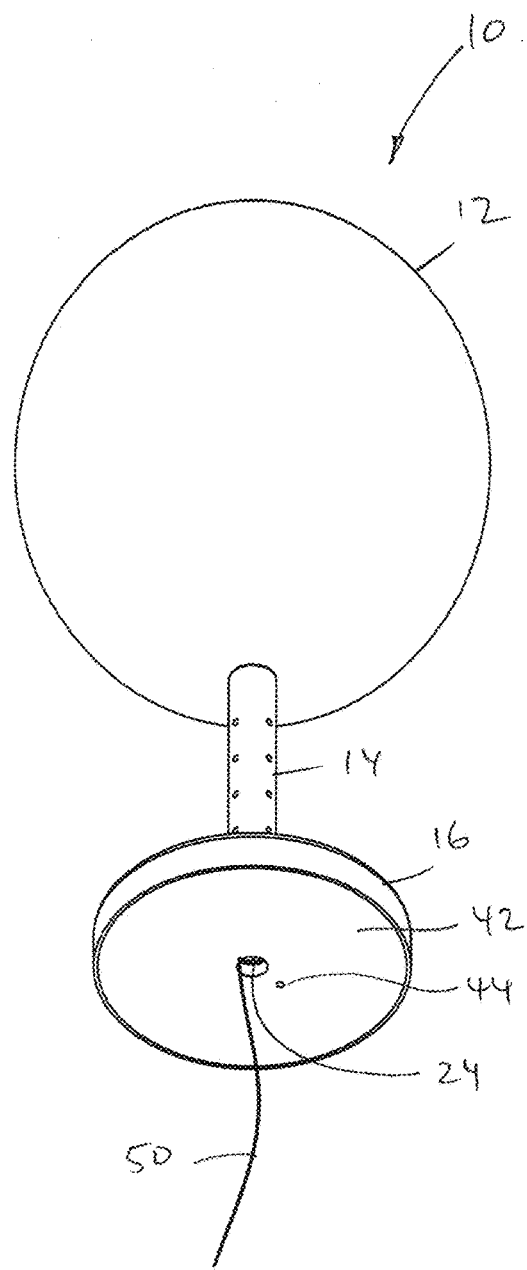
FIG. 5 is a bottom perspective view of the agent delivery device in the expanded configuration.
Figure 6:
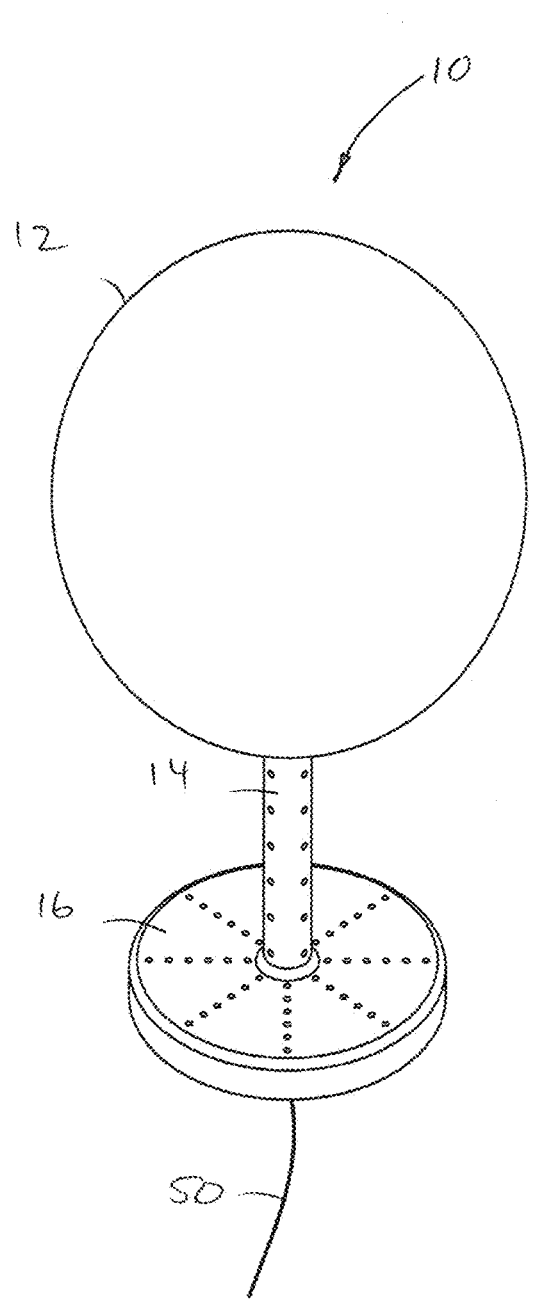
FIG. 6 is a top perspective view of the agent delivery device in the expanded configuration.

A tether 50 extends from the valve 24 and out of the proximal end of the device. The tether 50 is attached to a leaflet of the valve 24 and operates to open the valve to release the inflation member from the balloon. The tether 50 also operates as a security device for the removal of the device from the patient. Referring to FIG. 26, as an alternative to tether 50, a deflectable tab 950 may be integrated with bumper 16'. When the free end 952 of the tab 950 is pressed, the tab 950 includes internal structure (not shown) that interacts with the valve 24 (not shown) to open the valve; e.g., by deforming one of the valve leaflets. The free end 952 of the tab 950 may include raised ridges 954 so that it can be readily identified by user's touch when the device is inserted into the anus and not viewable.

Variations to the above described system are anticipated. Instead of filling the pores prior to implant, porous membrane 32 may be covered with an impermeable sheet 60 that is removed after the storage portion 30, 40 is filled with the agent and prior to inserting the device into the anal canal.

In another embodiment, the reservoir is filled after the device is inserted into the anal canal and the medicine is permitted to release immediately. In such case, no filler or cover is provided for the porous membrane.

Figure 14:
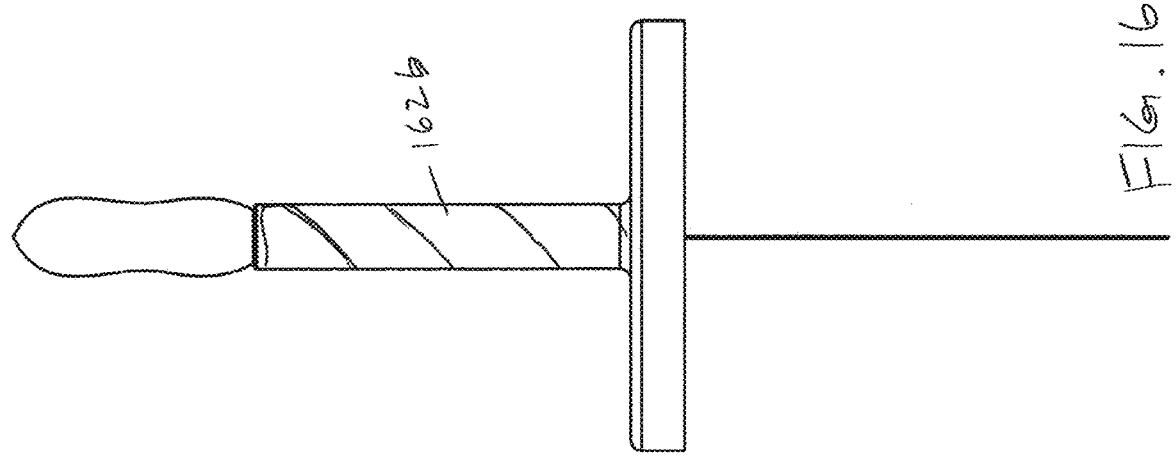
FIG. 14 is a side elevation of an agent delivery device in a collapsed configuration with the agent loaded in strips extending in a first direction about an exterior surface of the device.
Figure 15:
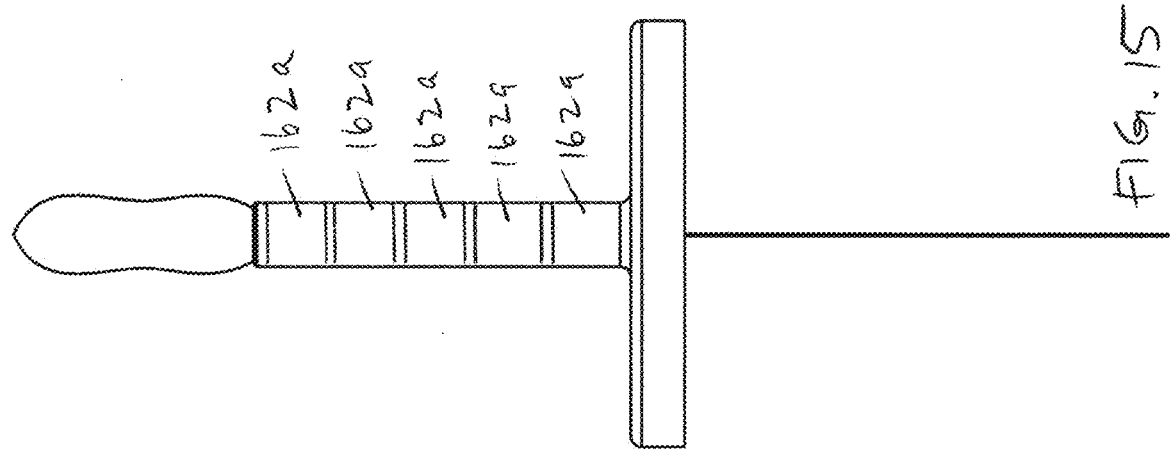
FIG. 15 is a side elevation of an agent delivery device in a collapsed configuration with the agent loaded in strips extending in a second direction about an exterior surface of the device.
Figure 16:
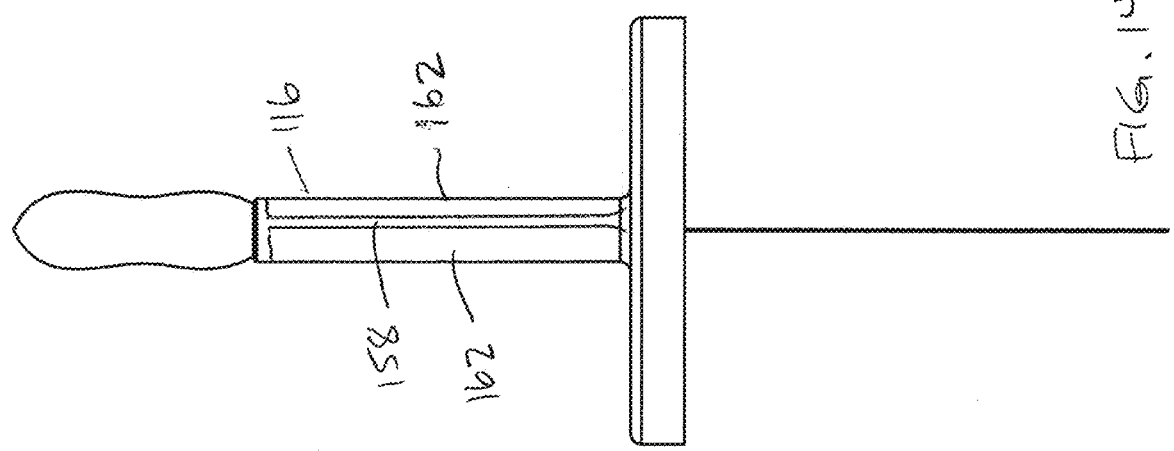
FIG. 16 is a side elevation of an agent delivery device in a collapsed configuration with the agent loaded in strips extending in a third direction about an exterior surface of the device.

Turning now to FIG. 15, in another embodiment, the storage portion is defined by an external surface area 158 of the shaft 116 and the agent is applied to the external surface of the shaft. The agent may be loaded in strips 162 that can be attached to the external surface to the shaft and tissue-contacting surface of the bumper prior to insertion of the device. The strips may include a diffusible form of the agent, similar to a transdermal patch. The strips 162 may include adhesive backing 164 for such application. The strips 162 may be provided separately from the device, and applied by the patient to the device prior to insertion, or the strips may be pre-attached to the device. The strips 162 may be loaded with one or more therapeutic agents, or strips with different agents can be separately supplied. The strips 162 can be applied longitudinally (FIG. 14), applied circumferentially (strips 162a in FIG. 15), or applied in a helical arrangement (strips 162b in FIG. 16).

Figures 17, 18:
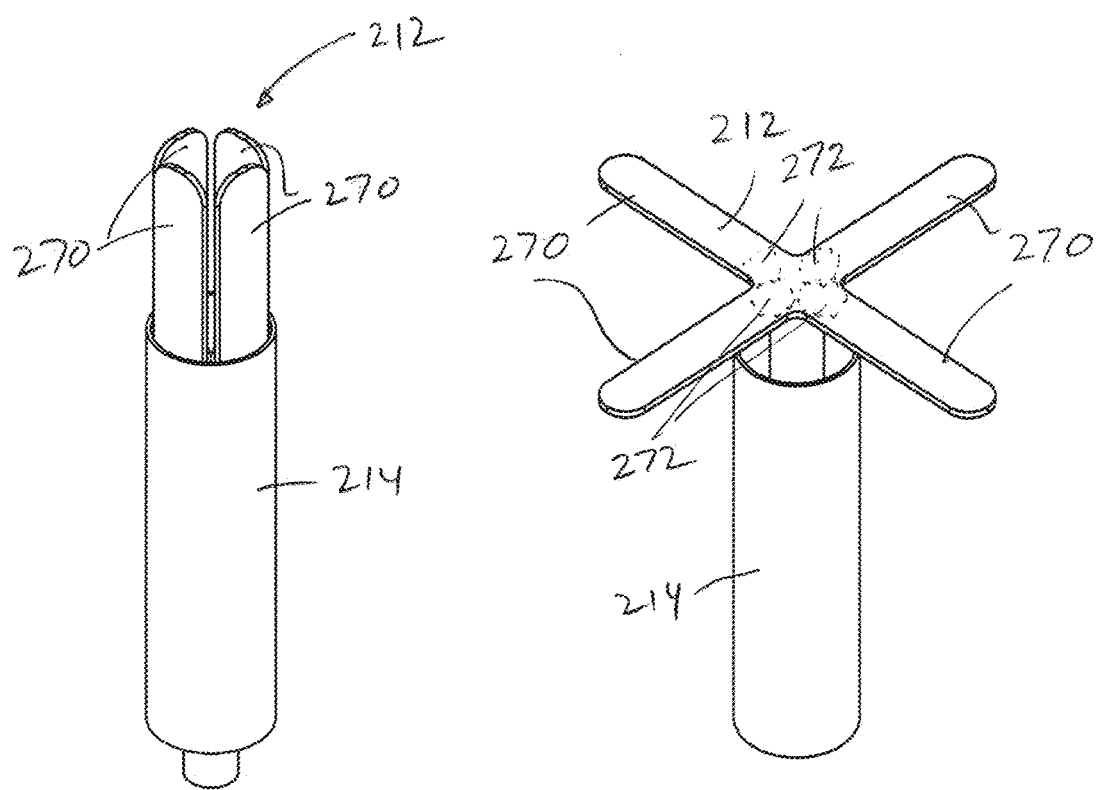
FIG. 17 is a top perspective view of another embodiment of an anchor member of an agent delivery device in a collapsed configuration.
FIG. 18 is a top perspective view of the anchor member of FIG. 17 in an expanded configuration.

Referring now to FIGS. 17 and 18, another exemplar embodiment of a deployable anchor 212 for the device is shown. The deployable anchor 212 includes a plurality of resilient retainers 270 that are stored or positioned in the shaft 214 during insertion of the device into the anal canal, and then deployed out of the shaft into an expanded state upon full insertion. The retainers 270 may be a silicone, a non-irritating polymer, a spring metal, or a heat-activated shape memory. The deployment may be effected by user-applied force to longitudinally displace a spring-release hinge 272 of the retainer beyond the distal end of the shaft 214, heat-activation, or other means. Then, when it is necessary to remove the device, an opposing force is applied to collapse the retainers back into the shaft.

Figures 19, 20:
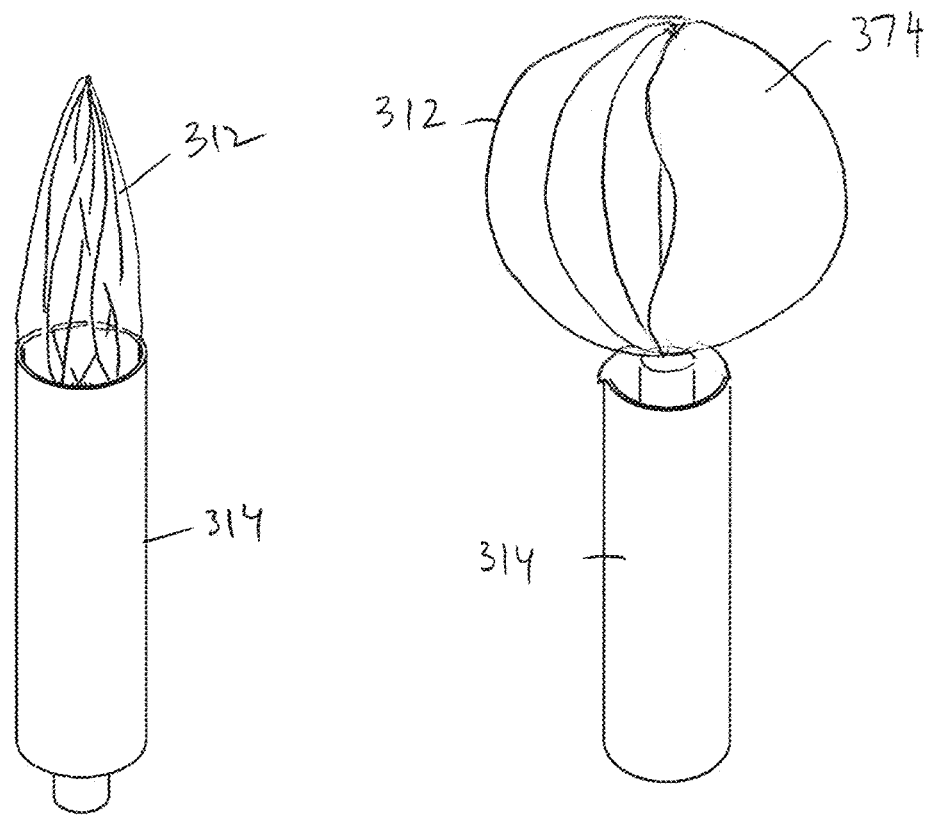
FIG. 19 is a top perspective view of another embodiment of an anchor member of an agent delivery device in a collapsed configuration.
FIG. 20 is a top perspective view of the anchor member of FIG. 19 in an expanded configuration.

Turning now to FIGS. 19 and 20, yet another exemplar embodiment of a deployable anchor for the device is shown. The anchor includes a self-expanding basket 312 that is stored in the shaft 314 and when advanced distally out of the shaft expands into a larger diameter anchoring configuration (FIG. 20). The basket may be optionally covered with a sheet material 374, such that it operates as a self-expanding balloon. The basket may be made from resilient plastic or a superelastic metal alloy.

In the embodiments shown in FIGS. 17 through 20, the device does not require an inflation valve.

Figure 21:
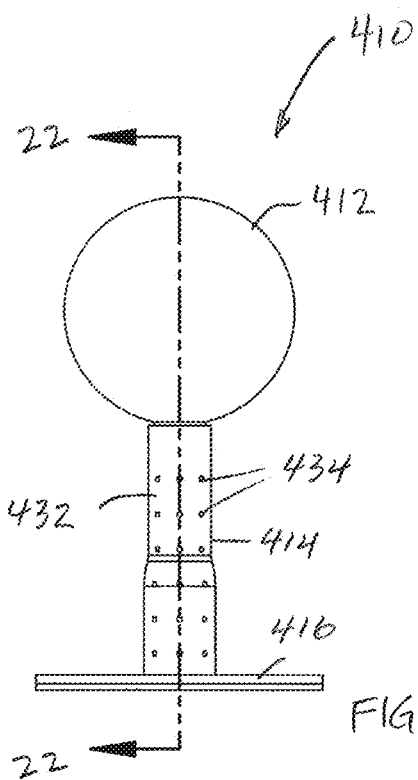
FIG. 21 is a side elevation of another embodiment of an agent delivery device.
Figure 22:
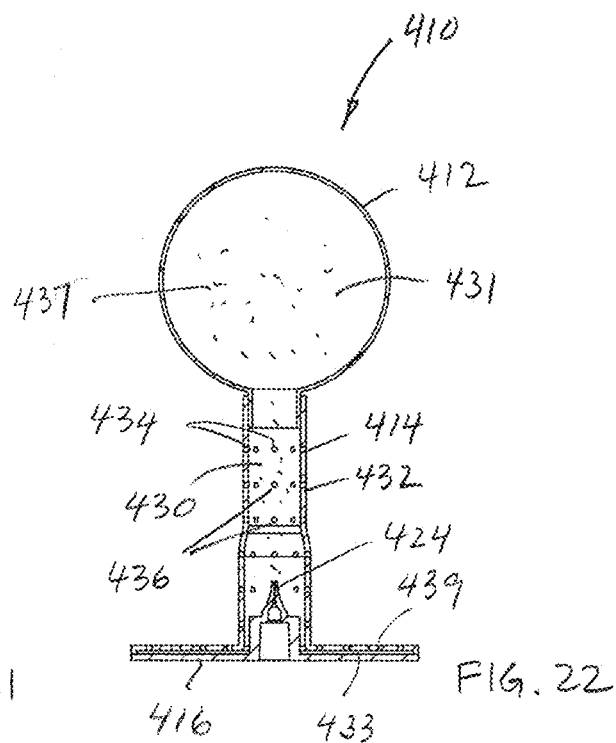
FIG. 22 is a longitudinal section view of the device of FIG. 21 across line 22-22.

Referring now to FIGS. 21 and 22, another embodiment, substantially similar to the device shown in FIGS. 1 through 4, is shown. The device 410 includes an inflatable anchor 412, a shaft 414, and a bumper 416. The shaft 412 includes an interior agent storage volume 430 open to communicate with a primary agent storage volume 431 within the anchor 412. The bumper 416 includes an additional storage volume 433 in fluid communication with the agent storage volume 430. A one-way valve 424 is provided into the interior volume 430 of the shaft 414, preferably at or adjacent the bumper 416. An outer wall 432 of the shaft 414 includes a plurality of pores 434, and a tissue-contacting surface of the bumper also includes pores 439. The pores 434, 439 are filled with a meltable, dissolvable, bioabsorable or other releasable material 436 that temporarily prevents release of agent from within storage volumes 430, 431 to outside the device 410. In use, the device 410 is inserted into the anus, and a flowable agent 437 is injected through the shaft 414 and into the balloon anchor 412 to sufficiently inflate the anchor 412 to retain the device in the anus. Then, at a determined rate, the filler material 436 in the pores 434 of the outer wall 432 melts, dissolves or is otherwise removed in situ to permit the agent 437 to be dispensed from the pores over a short period of time. Different types of filler materials 436 may be used in different holes of the device in order to open select pores at different rates and times. The pores 434 are sufficiently small that even when opened, a measured flow rate of agent from inside the device to outside the device and into the anus is provided. The release rate is controlled by the size of the opening of the pore 434, the rate of melting, absorption, or dissolution of the filler material 436, the viscosity of the agent 437, and the contractile force of the balloon anchor 412 on the agent 437, as contraction of the anchor forces the agent 437 through the pores 434. Once the storage portion 431 of the anchor 412 is depleted of agent 435 and collapsed inward, the device 410 is automatically releasable from the anus.

Figure 23:
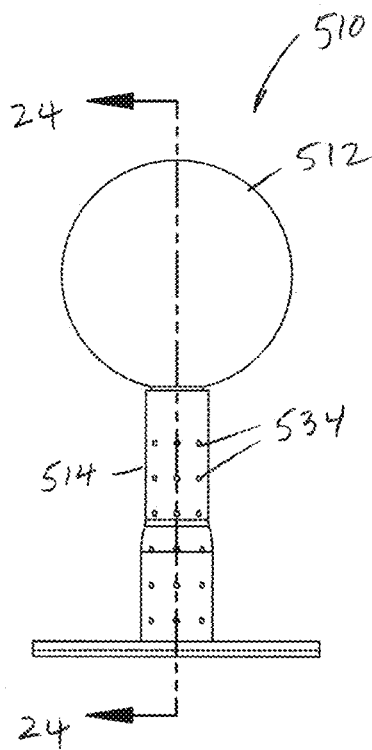
FIG. 23 is a side elevation of another embodiment of an agent delivery device.
Figure 24:
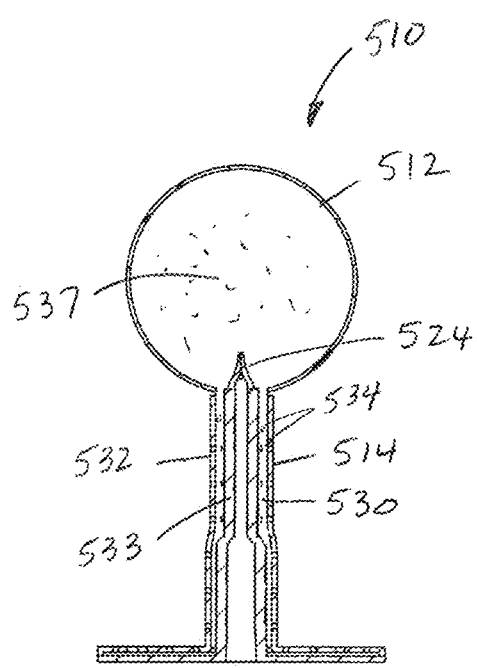
FIG. 24 is a longitudinal section view of the device of FIG. 23 across line 24-24.

Turning now to FIGS. 23 and 24, another embodiment of a device 510 substantially similar to the embodiment shown in FIGS. 21 and 22 is provided. The device 510 is distinguished from device 410 in that the shaft 514 includes an inner tubular wall 533 within its outer wall 532, and the valve 524 is provided at or adjacent the boundary between the shaft 514 and the anchor 512. The device 510 is filled with agent 537 in a manner similar to device 410, with the agent 537 stored in the storage volume 531 of the anchor 512, as well as the ring-shaped space 530 (in cross-sectional shape) defined between the inner and outer tubular walls 532, 533. As filler located in the pores of the outer wall 532 melts, dissolves, or is otherwise released, the contractile force of the expanded anchor 512 forces the agent into the toroidal space 530 and out of the pores 534 at a designed rate. Once the anchor 512 is depleted of agent 537 and collapsed, the device 510 is automatically releasable from the anus.

Figure 25:
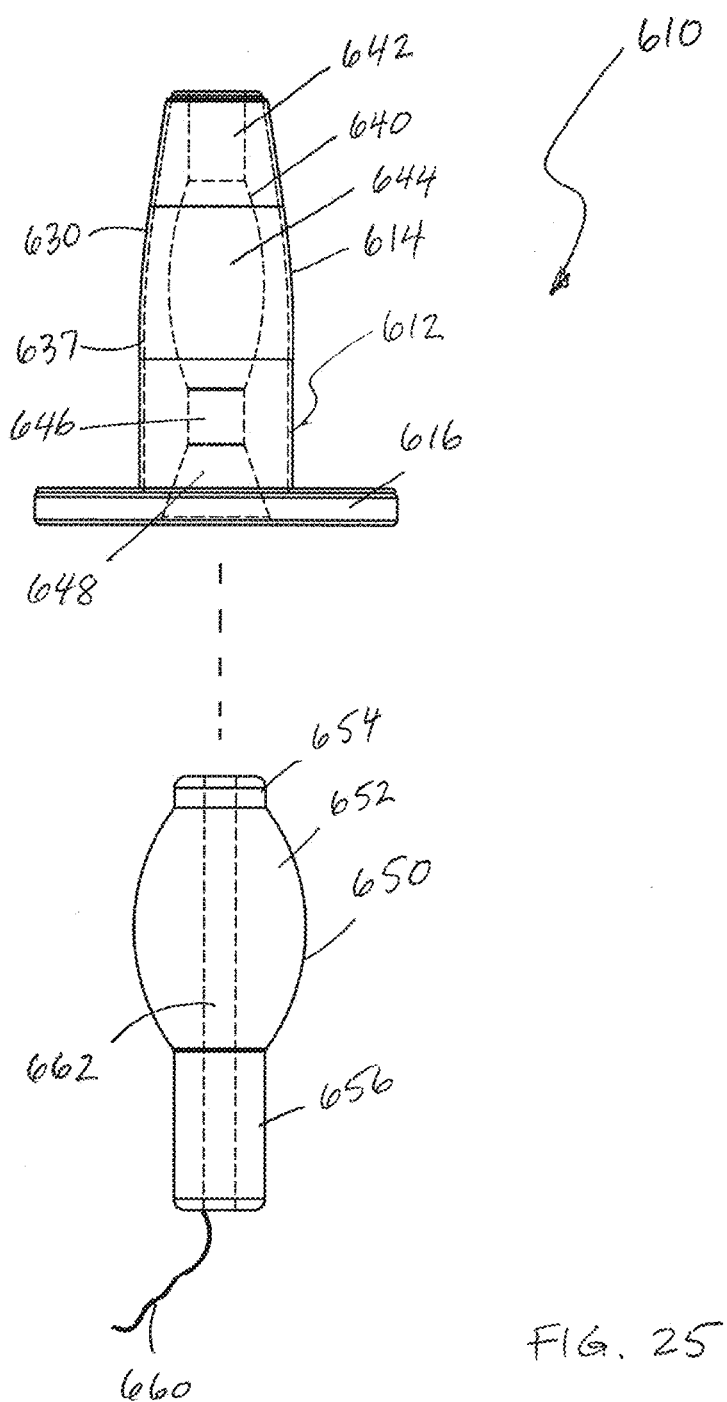
FIG. 25 is an assembly view of another embodiment of an agent delivery device.

Referring now to FIG. 25, another embodiment of a device 610 for releasing an agent into the anal and perianal region is shown. The device 610 includes a deformable silastic plug 612 and a core element 650. The plug 612 forms a shaft 614 and a bumper 616. The shaft 614 has an outer surface 630 provided with a coating or other releasable layer 637 of an agent. The plug 612 includes an inner bore 640 having a distal first cylindrical portion 642, an ovoid second portion 644 having one end communicating with the first portion, a third cylindrical portion 646 extending from an opposite end of the second portion, and a proximal frusto-conical fourth portion 648 extending from the third portion and having its largest diameter opening at the bumper. The core element 650 is provided for insertion into the inner bore 640. The core element 650 includes a bulbous portion 652 adapted to be inserted within the ovoid portion 644 of the inner bore, a distal first cylindrical tip 654 adapted to enter the first cylindrical portion 642, and a proximal second cylindrical portion 656 adapted to reside within the third and fourth portions 646, 648 of the bore. The bulbous portion 652 is preferably larger in diameter than the ovoid portion 644 of the bore such that it is adapted to deformably expand the plug 612 when the core element 650 is inserted into the inner bore 640. In use, the plug 612 with agent 637 thereon is inserted into the anus; then the core element 650 is inserted into the inner bore 640 to enlarge the diameter of the plug 612 and provide retention. The retained plug 612 is placed in the anus until the agent is 637 released from the surface 630 of the plug 612. A tether 660 is preferably coupled to a proximal end of the core element to aid in removal of the core element and subsequent release of the plug. Alternatively, a bumper (as shown with respect to the plug) may be integrated with the core element to aid in its removal. The core element 650 optionally includes lumen 662 to vent gas while the device is in use.

It is anticipated that the device will be used to treat anal fissures and/or hemorrhoids. For such treatment, the agent can include one or more of a pain relief agent, an anti-inflammatory agent, and a muscle relaxant. It is further anticipated that the device can be used to deliver drugs systemically, particularly where a patient's condition indicates that the anal mucosa and underlying vasculature may be a suitable pathway for delivery of the agent. By way of example, such agents may include pain relivers, fever reducers, and anesthetics. Additionally, any agent currently delivered via suppositories can be delivered by the device described herein. Moreover, natural substances and nutrients in refined and unrefined forms (e.g., herbal tinctures, extracts, solutions, oils, and foods) can be used to treat conditions of the anus and rectum, as well as systemic conditions or needs via trans-anal and rectal absorption. By way of example only, aloe vera gel and cannabinoid oils can be delivered. By way of further example, it is anticipated that the device also can be used to deliver systemic therapeutic and non-therapeutic agents, including natural substances, nutrients, foods, and medications, to patients that are unconscious, such as those that are in a coma, or otherwise unsuitable for oral and/or intravenous administration. In one method of delivering a systemic agent to an unconscious patient, a device for delivery of an agent to anal and/or perianal tissues of the patient is provided with the agent and inserted into the anus of the patient. The agent may be provided loaded into or on the device or in a separate container that can be used to fill the device pre- or post-insertion into the anus. A portion of the device is expanded to anchor the device until a dose of the agent has been delivered to the anal and/or perianal tissues. Then the device is removed from the anus of the patient.

There have been described and illustrated herein several embodiments of an agent delivery device for use in the anal canal and methods of treatment. While particular embodiments of the invention have been described, it is not intended that the invention be limited thereto, as it is intended that the invention be as broad in scope as the art will allow and that the specification be read likewise. Thus, it is intended that the disclosure include each of the several embodiments provided with a tether or tab for valve release (and device removal, in the case of the tether); various therapeutic, non-therapeutic or combinations of agents, and different types of anchors, where appropriate. In addition, it is intended that each of the embodiments is also provided with in a dedicated suitable kit form. Further, it is intended that all of the embodiment be provided in any suitable sizes and shapes appropriate to treatment for various adult, child and other mammalian populations. It will therefore be appreciated by those skilled in the art that yet other modifications could be made to the provided invention without deviating from its scope.

What is claimed is:

1. A delivery device for a flowable agent to an anus, comprising:
    a) a hollow shaft having a proximal end, a distal end, and defining a longitudinal axis between its proximal and distal ends and a diameter transverse to its longitudinal axis, the shaft defining a first storage volume for an agent to be delivered to anal or perianal tissues, the shaft including a wall having pores through which the agent is released from the first storage volume, and the pores filled with heat-activated material that releases to open the pores after the shaft is inserted into the anus;
    b) an inflatable anchor at the distal end of the shaft for insertion into the anus, the inflation anchor having an expanded configuration greater in dimension than the diameter of the shaft;
    c) a bumper at the proximal end of the shaft, the bumper having a dimension transverse to the longitudinal axis to prevent uncontrolled ingress of the shaft and anchor within the anus;
    d) a one-way valve integrated with the device and through which to inject an inflation medium through the into the anchor; and
    e) a release element coupled to the valve and extending from the bumper, wherein force applied to the release element opens the one-way valve to release inflation medium within the anchor.

2. The device according to claim 1, wherein:
the bumper defines a second storage volume.

3. The device according to claim 2, wherein:
the first and second storage volumes are at an interior of the device and in fluid communication with each other such that the flowable agent can flow between the first and second storage volumes.

4. The device according to claim 2, wherein:
the second storage volume is at an interior of the bumper, and the bumper includes a surface having additional pores through which the agent is released from the second storage volume, wherein the first and second storage volumes are in fluid communication.

5. The device according to claim 1, wherein:
the inflatable anchor and the storage volume are separated from fluid communication.

6. The device according to claim 1, further comprising:
the agent provided to the first storage volume, wherein the agent includes one or more of a pain relief agent, an anti-inflammatory agent, and a muscle relaxant.

7. The device according to claim 1, further comprising:
the agent provided to the first storage volume, wherein the agent is adapted to provide pain relief, anti-inflammatory properties, and muscle relaxation.

8. The device according to claim 1, further comprising:
the agent provided to the first storage volume, wherein the agent comprises a natural sub stance.

9. The device according to claim 1, wherein the release element is a tether.

10. The device according to claim 1, wherein the release element is a tab integrated with the bumper.

11. A device for delivery of a flowable agent to the anus and perianal tissue, comprising:
 a) an elastic anchor having a first interior adapted to be filled with the flowable agent, the anchor expanded from a first configuration to an enlarged second configuration upon being filled with the agent;
 b) a shaft having an outer wall with pores, the wall at least partly defining a second interior adapted to receive the agent from the interior of the anchor and release the agent to the anal tissue, the first interior of the anchor in fluid communication with the second interior of the shaft, the pores including a dissolvable filler that blocks the pores, the filler adapted to dissolve out of the pores after the shaft is inserted into the anus;
 c) an external bumper that externally anchors the device to prevent uncontrolled inward migration of the device; and
 d) a one-way valve integrated with the device and through which to inject the agent into the interior of the anchor, wherein when the anchor is expanded with the agent, a contractile force of the anchor urges the agent into the second interior of the shaft and out of the pores of the wall.

12. The device according to claim 11, wherein:
the bumper includes a third interior in fluid communication with the second interior, and porous adapted to release the flowable agent from the third interior to the perianal tissue.

13. The device according to claim 11, wherein:
the valve is located at or adjacent the bumper.

14. The device according to claim 11, wherein:
the valve is located at or adjacent the anchor.

15. The device according to claim 11, wherein:
the shaft includes an inner tubular wall, such that the second interior has a ring-shaped cross-section.

16. A device for insertion into an anus for delivery of an agent to anal and perianal tissue, comprising:
 a) an expandable anchor expandable from a first configuration to an enlarged diameter second configuration;
 b) a shaft having an outer wall provided with pores, the pores filled with a releasable material that automatically releases when the shaft is placed within the anus, the shaft at least partly defining a storage volume adapted to receive the agent and dispense the agent through the pores and into the anal tissue;
 c) an external bumper that externally anchors the device to prevent uncontrolled inward migration of the device; and
 d) a one-way valve integrated with the device and through which to inject the agent into the storage volume.

17. The device according to claim 16, wherein:
the storage volume is further comprised by an interior of the expandable anchor.

18. The device according to claim 16, wherein:
wherein when the storage volume is filled with the agent, a force from the anchor urges the agent from the storage volume and out of the pores.

19. The device according to claim 17, wherein:
The bumper includes a porous wall in fluid communication with the storage volume and through which the agent is dispensed.

20. A device for delivery of an agent to an anus, comprising:
 a) a hollow shaft having a proximal end, a distal end, and defining a longitudinal axis between its proximal and distal ends and a diameter transverse to its longitudinal axis, the outer surface of the shaft provided with a first storage volume for an agent to be delivered to anal or perianal tissues, the first storage volume in the form of adhesive strips loaded with the agent;
 b) an inflatable anchor at the distal end of the shaft for insertion into the anus, the inflation anchor having an expanded configuration greater in dimension than the diameter of the shaft;
 c) a bumper at the proximal end of the shaft, the bumper having a dimension transverse to the longitudinal axis to prevent uncontrolled ingress of the shaft and anchor within the anus;
 d) a one-way valve integrated with the device and through which to inject an inflation medium through the into the anchor; and
 e) a release element coupled to the valve and extending from the bumper, wherein force applied to the release element opens the one-way valve to release inflation medium within the anchor.

\* \* \* \* \*